United States Patent
Yang et al.

(10) Patent No.: US 10,308,753 B2
(45) Date of Patent: Jun. 4, 2019

(54) IONIC DIOL, ANTISTATIC POLYURETHANE, AND METHOD OF MAKING THE SAME

(71) Applicant: 3M INNOVATIVE PROPERTIES COMPANY, St. Paul, MN (US)

(72) Inventors: Yu Yang, Eden Prairie, MN (US); Jason M. Kehren, Stillwater, MN (US); Yongshang Lu, Woodbury, MN (US); Suresh S. Iyer, Woodbury, MN (US); William M. Lamanna, Stillwater, MN (US); Thomas P. Klun, Lakeland, MN (US); Jeffrey A. Peterson, Hugo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 161 days.

(21) Appl. No.: 15/532,881

(22) PCT Filed: Dec. 8, 2015

(86) PCT No.: PCT/US2015/064389
§ 371 (c)(1),
(2) Date: Jun. 2, 2017

(87) PCT Pub. No.: WO2016/099995
PCT Pub. Date: Jun. 23, 2016

(65) Prior Publication Data
US 2017/0355805 A1 Dec. 14, 2017

Related U.S. Application Data

(60) Provisional application No. 62/092,558, filed on Dec. 16, 2014.

(51) Int. Cl.
| | | |
|---|---|---|
| *C08K 5/00* | (2006.01) | |
| *C08K 5/19* | (2006.01) | |
| *C08G 18/08* | (2006.01) | |
| *C08G 18/32* | (2006.01) | |
| *C08G 18/38* | (2006.01) | |
| *C08G 18/40* | (2006.01) | |
| *C08G 18/44* | (2006.01) | |
| *C08G 18/48* | (2006.01) | |
| *C08G 18/75* | (2006.01) | |
| *C07C 219/06* | (2006.01) | |
| *C07C 229/30* | (2006.01) | |
| *C07C 307/06* | (2006.01) | |
| *C07C 311/48* | (2006.01) | |
| *C09D 175/04* | (2006.01) | |
| *D06M 15/576* | (2006.01) | |

(52) U.S. Cl.
CPC ........ *C08G 18/0814* (2013.01); *C07C 219/06* (2013.01); *C07C 229/30* (2013.01); *C07C 307/06* (2013.01); *C07C 311/48* (2013.01); *C08G 18/3206* (2013.01); *C08G 18/3819* (2013.01); *C08G 18/3861* (2013.01); *C08G 18/4018* (2013.01); *C08G 18/44* (2013.01); *C08G 18/4833* (2013.01); *C08G 18/758* (2013.01); *C08K 5/0075* (2013.01); *C08K 5/19* (2013.01); *C09D 175/04* (2013.01); *D06M 15/576* (2013.01)

(58) Field of Classification Search
CPC ............ C08G 18/0814; C08G 18/3861; C08G 18/44; C08G 18/4018; C08G 18/758; C08G 18/4833; C08G 18/3819; C08G 18/3206; D06M 15/576; C08K 5/19; C08K 5/0075; C09D 175/04
See application file for complete search history.

(56) References Cited

U.S. PATENT DOCUMENTS

| | | | |
|---|---|---|---|
| 3,641,199 A | 2/1972 | Niederhauser | |
| 3,700,643 A | 10/1972 | Smith | |
| 3,887,450 A | 6/1975 | Gitano | |
| 3,895,949 A | 7/1975 | Akamatsu | |

(Continued)

FOREIGN PATENT DOCUMENTS

| | | |
|---|---|---|
| CN | 101768884 | 7/2010 |
| CN | 103319683 A | 9/2013 |

(Continued)

OTHER PUBLICATIONS

International Search Report for PCT International Application No. PCT/US2015/064389, dated Apr. 11, 2016, 5 pages.

*Primary Examiner* — Rabon A Sergent
(74) *Attorney, Agent, or Firm* — Bradford B. Wright

(57) ABSTRACT

An ionic diol has formula wherein $R^1$ represents an alkyl group having from 6 to 18 carbon atoms; $R^2$ and $R^3$ independently represent alkyl groups having from 1 to 4 carbon atoms; $R^4$ represents an alkylene group having from 2 to 8 carbon atoms; and $R^5$ represents an alkylene group having from 1 to 8 carbon atoms. Antistatic polymers are formed by copolymerization of monomers including a diisocyanate, an ionic diol, a polyether diol, and at least one non-ionic diols. Methods of making the antistatic polyurethanes are also disclosed.

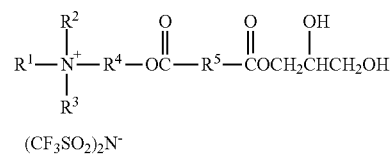

23 Claims, No Drawings

(56) References Cited

U.S. PATENT DOCUMENTS

| | | |
|---|---|---|
| 3,931,117 A | 1/1976 | Leonard |
| 5,039,733 A | 8/1991 | Dormish et al. |
| 6,147,155 A | 11/2000 | Yonek et al. |
| 6,372,829 B1 | 4/2002 | Lamanna |
| 6,495,243 B1 | 12/2002 | Malhotra |
| 6,592,988 B1 | 7/2003 | Thompson |
| 6,706,920 B2 | 3/2004 | Lamanna |
| 6,740,413 B2 | 5/2004 | Klun |
| 6,784,237 B2 | 8/2004 | Thompson |
| 6,924,329 B2 | 8/2005 | Klun |
| 7,361,706 B2 | 4/2008 | Thompson |
| 7,678,941 B2 | 3/2010 | Savu |
| 8,449,970 B2 | 5/2013 | Pellerite |
| 2003/0114560 A1 | 6/2003 | Yang |
| 2011/0021691 A1 | 1/2011 | Chiang |
| 2012/0288675 A1 | 11/2012 | Klun |

FOREIGN PATENT DOCUMENTS

| | | |
|---|---|---|
| FR | 2976486 | 12/2012 |
| JP | 2005-120158 | 5/2005 |
| JP | 2006-036885 | 2/2006 |
| JP | 2007-009042 | 1/2007 |
| JP | 2009-091390 | 4/2009 |
| JP | 2009-144051 | 7/2009 |
| JP | 2012-057110 | 3/2012 |
| WO | WO 2011-031442 | 3/2011 |
| WO | WO 2013-166198 | 11/2013 |
| WO | WO 2016-099948 | 6/2016 |
| WO | WO 2016-099996 | 6/2016 |

IONIC DIOL, ANTISTATIC POLYURETHANE, AND METHOD OF MAKING THE SAME

TECHNICAL FIELD

The present disclosure broadly relates to antistatic polymers and methods of making them.

BACKGROUND

Antistats or antistatic agents are used to dissipate electrostatic or static charge. Electrostatic charge buildup is responsible for a variety of problems in the processing and the use of many industrial products and materials. Electrostatic charging can cause materials to stick together or to repel one another. In addition, static charge buildup can cause objects to attract dirt and dust that can lead to fabrication or soiling problems and can impair product performance. Sudden electrostatic discharges from insulating objects can also be a serious problem. When flammable materials are present, a static electric discharge can serve as an ignition source, resulting in fires and/or explosions.

Electrostatic charge is a particular problem in the electronics industry, because modern electronic devices are extremely susceptible to permanent damage by electrostatic discharges. The buildup of electrostatic charge on insulating objects is especially common and problematic under conditions of low humidity and when liquids or solids move in contact with one another (tribocharging).

Static charge build-up can be controlled by increasing the electrical conductivity of a material. This can be accomplished by increasing ionic or electronic conductivity. The most common means of controlling static accumulation today is by increasing electrical conductivity through moisture adsorption. This is commonly achieved by adding moisture to the surrounding air (humidification) or by the use of hygroscopic antistatic agents, which are generally referred to as humectants because they rely on the adsorption of atmospheric moisture for their effectiveness. Most antistatic agents operate by dissipating static charge as it builds up; thus, static decay rate and surface conductivity are common measures of the effectiveness of antistatic agents. Antistatic agents can be applied to the surface (external antistatic agent) or incorporated into the bulk (internal antistatic agent) of the otherwise insulating material. Internal antistatic agents are commonly employed in polymers such as plastics.

Generally, internal antistatic agents fall into one of the following classes: (1) ones that are mixed directly into a molten polymer during melt processing; (2) ones that are mixed into a polymer solution, coated, and dried, or (3) ones that dissolve into a monomer (with or without a solvent) that is subsequently polymerized.

Antistatic agents are known and used over a broad range of chemical classes, including organic amines and amides, esters of fatty acids, organic acids, polyoxyethylene derivatives, polyhydric alcohols, metals, carbon black, semiconductors, and various organic and inorganic salts. Many are also surfactants and can be neutral or ionic in nature. Many low molecular weight, neutral antistatic agents have sufficiently high vapor pressures and thus are unsuitable for use at high temperatures (e.g., polymer melt processing) due to material losses that occur via evaporation. Many other neutral antistatic agents have insufficient thermal stability to survive polymer melt processing or other high temperature processing conditions.

Most non-metallic antistatic agents are generally humectants that rely on the adsorption and conductivity of water for charge dissipation. Thus, their effectiveness is typically diminished at low atmospheric humidity. Because many of these antistatic agents are also water-soluble, they are easily removed by exposure of the material to water (e.g., washing) and therefore are not very durable.

Metal salts of inorganic, organic, and fluoroorganic anions are also useful as antistatic agents in certain polymer compositions. Alkali metal salts are most commonly used due to cost and toxicity considerations and to the high affinity of alkali metal cations, especially lithium, for water. However, most metal salts are not compatible with polymers of moderate to low polarity, such as polypropylene, polyester, and polycarbonate. This incompatibility can result in inadequate antistatic agent performance and/or an unacceptable reduction in physical properties or transparency in a finished polymeric article. Consequently, the use of metal salts as internal antistatic agents is generally limited to highly polar and/or hydrophilic polymer matrices.

SUMMARY

There is a continuing need for antistatic agents, and especially antistatic agents that can be incorporated into coatings and polymer melt compositions.

In one aspect, the present disclosure provides an ionic diol represented by the formula:

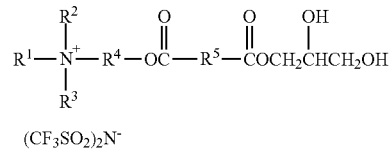

wherein
$R^1$ represents an alkyl group having from 6 to 18 carbon atoms;
$R^2$ and $R^3$ independently represent alkyl groups having from 1 to 4 carbon atoms;
$R^4$ represents an alkylene group having from 2 to 8 carbon atoms; and
$R^5$ represents an alkylene group having from 1 to 8 carbon atoms.

In another aspect, the present disclosure provides an antistatic polyurethane having a polymer backbone comprising:
at least one divalent segment a) represented by the formula

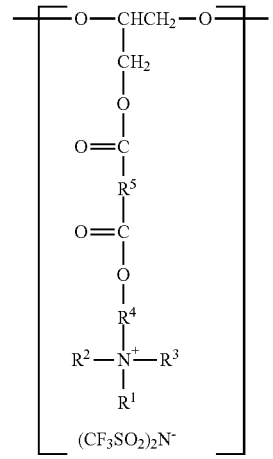

wherein
R$^1$ represents an alkyl group having from 6 to 18 carbon atoms,
R$^2$ and R$^3$ independently represent alkyl groups having from 1 to 4 carbon atoms,
R$^4$ represents an alkylene group having from 2 to 18 carbon atoms, and
R$^5$ represents an alkylene group having from 2 to 18 carbon atoms; divalent segments b) represented by the formula

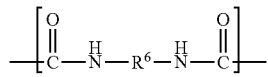

wherein
R$^6$ represents a divalent organic group having from 2 to 18 carbon atoms, wherein at least one of the divalent segments b) is adjacent to at least one of the divalent segments a);
divalent segments c) represented by the formula

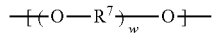

wherein
R$^7$ represents a divalent organic group having from 2 to 12 carbon atoms, and
w represents a positive integer, wherein at least one of the divalent segments c) is adjacent to at least one of the divalent segments b); and
divalent segments d) represented by the formula

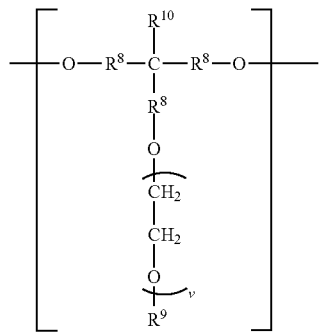

wherein
each R$^8$ independently represents an alkylene group having from 1 to 8 carbon atoms,
each R$^9$ independently represents an alkyl group having from 1 to 4 carbon atoms,
each R$^{10}$ independently represents H or an alkyl group having from 1 to 8 carbon atoms, and
v represents a positive integer, wherein at least one of the divalent segments d) is adjacent to at least one of the divalent segments b), wherein terminal carbonyl groups on adjacent divalent segments are not directly bonded to each other, and wherein terminal —O— groups on adjacent divalent segments are not directly bonded to each other.

In a third aspect, the present disclosure provides a method of making an antistatic polyurethane, the method comprising steps:

a) reacting a first diol with a molar excess of a diisocyanate to form a first prepolymer, wherein the first diol is represented by the formula

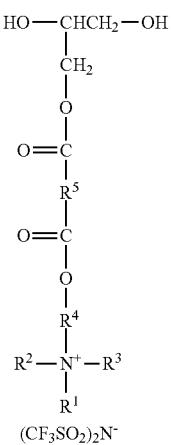

wherein
R$^1$ represents an alkyl group having from 6 to 18 carbon atoms;
R$^2$ and R$^3$ independently represent alkyl groups having from 1 to 4 carbon atoms;
R$^4$ represents an alkylene group having from 2 to 18 carbon atoms
R$^5$ represents an alkylene group having from 2 to 18 carbon atoms; and
wherein the diisocyanate is represented by the formula

OCN—R$^6$—NCO wherein R$^6$ represents a divalent organic group having from 2 to 18 carbon atoms;

b) reacting the first prepolymer with a second diol to form a second prepolymer, wherein the second diol is represented by the formula

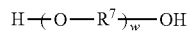

wherein
R$^7$ represents a divalent organic group having from 2 to 12 carbon atoms,
w represents a positive integer; and c) reacting the second prepolymer with a third diol to form the antistatic polyurethane,
wherein the third diol is represented by the formula

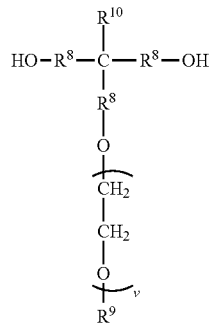

wherein
each $R^8$ independently represents an alkylene group having from 1 to 8 carbon atoms,
each $R^9$ independently represents an alkyl group having from 1 to 4 carbon atoms,
each $R^{10}$ independently represents H or an alkyl group having from 1 to 8 carbon atoms, and
v represents a positive integer.

In a fourth aspect, the present disclosure provides antistatic polyurethanes made according to methods of making an antistatic polyurethane according to the present disclosure.

When formulated into water-based coating compositions, antistatic polyurethanes according to the present disclosure may exhibit good dispersibility in water. Additionally, they may be uniformly incorporated into a variety of polymer melt compositions.

Antistatic polyurethanes according to the present disclosure may be used to provide coatings having static decay times of less than 7 seconds, and may impart a degree of protection due to their durability.

The properties of the antistatic polyurethanes of the present disclosure can be relatively easily tuned by adjustment of ratios of the polyol and polyisocyanate. For example, glass transition temperature ($T_g$), which also affects antistatic performance, can be modified by the percentage of both the surfactant diol and polypropylene glycol in the formulation. Antistatic polyurethane according to the present disclosure are useful; for example, in water-based coating compositions and as antistatic additives in polymer extrusion processes.

Features and advantages of the present disclosure will be further understood upon consideration of the detailed description as well as the appended claims.

DETAILED DESCRIPTION

Ionic diols according to the present disclosure are represented by the formula:

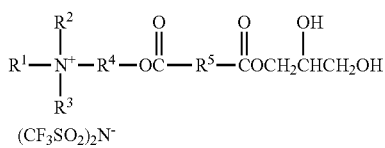

$R^1$ represents an alkyl group having from 6 to 18 carbon atoms, preferably 6 to 14 carbon atoms, more preferably 6 to 10 carbon atoms, and even more preferably 8 carbon atoms. Examples include hexyl, cyclohexyl, octyl, isooctyl, dimethylcyclohexyl, nonyl, decyl, dodecyl, hexadecyl, and octadecyl groups.

$R^2$ represents an alkyl group having from 1 to 4 carbon atoms. Examples include methyl, ethyl, n-propyl, isopropyl, and butyl groups. Preferably, $R^2$ represents a methyl or ethyl group.

$R^3$ represents an alkyl group having from 1 to 4 carbon atoms. Examples include methyl, ethyl, n-propyl, isopropyl, and butyl groups. Preferably, $R^2$ represents a methyl or ethyl group.

$R^4$ independently represents a linear alkylene group having from 2 to 4 carbon atoms. Examples include, ethylene (i.e., —CH$_2$CH$_2$—), propan-1,2-diyl (i.e., —CH$_2$CH(CH$_3$)—), propan-1,3-diyl, and butan-1,4-diyl groups. Preferably, $R^4$ represents ethan-1,2-diyl or propan-1,2-diyl.

$R^5$ represents an alkylene group having from 1 to 8 carbon atoms, preferably 2 to 4 carbon atoms. Examples include methylene, ethylene, propan-1,2-diyl, propan-1,3-diyl, butan-1,4-diyl groups, hexan-1,6-diyl, cyclohexan-1,4-diyl, and octan-1,8-diyl groups.

Antistatic polyurethanes according to the present disclosure comprise divalent segments a), b), and c), corresponding to the various components (e.g., polyols and polyisocyanates) used in their preparation. The divalent segments are arranged such that terminal carbonyl groups on adjacent divalent segments are not directly bonded to each other, and terminal —O— groups on adjacent divalent segments are not directly bonded to each other.

In some embodiments, the divalent segments a) are represented by the formula

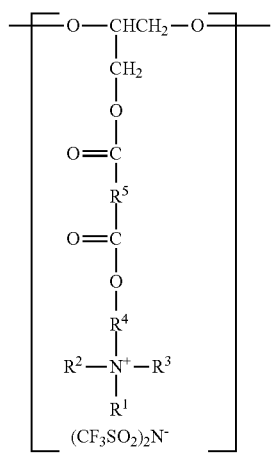

wherein $R^1$, $R^2$, $R^3$, $R^4$, and $R^5$ are as previously defined.

Divalent segments b) are represented by the formula

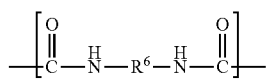

wherein $R^6$ represents a divalent organic group having from 2 to 18 carbon atoms, which may be, for example, a divalent residue of a diisocyanate (i.e., the divalent group remaining when the two —NCO groups are removed from the diisocyanate). In some preferred embodiments, $R^6$ represents a divalent organic group having from 6 to 16 carbon atoms, more preferably 12 to 16 carbon atoms. In some embodiments, $R^6$ represents a divalent organic group having from 2 to 12 carbon atoms, more preferably 4 to 8 carbon atoms.

Examples of suitable divalent organic groups include the divalent residues of the following diisocyanates; isophorone diisocyanate (IPDI); 4,4'-methylene-bis-phenylisocyanate (MDI); hexamethylene diisocyanate (HDI); 2,4-tolylene diisocyanate (TDI); bis(4-isocyanatocyclohexyl)methane (H-MDI); 3,5,5-trimethyl-1-isocyanato-3-isocyanatomethylcyclohexane); 1,3-bis(isocyanatomethyl)-cyclohexane. In some preferred embodiments, $R^6$ is hexan-1,6-diyl or methylene bis(cyclohexan-4-yl). Other diisocyanates are described, for example, in U.S. Pat. No. 3,641,199 (Niederhauser et al.); U.S. Pat. No. 3,700,643 (Potts et al.); and U.S. Pat. No. 3,931,117 (Potts et al.). Many suitable diisocyanates are available commercially (e.g., from Bayer Material- Science, Pittsburgh, Pa., or Dow Chemical Co., Midland, Mich.) and/or can be prepared by known methods.

Divalent segments c) are represented by the formula

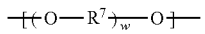

wherein $R^7$ represents a divalent organic group having from 2 to 12 carbon atoms, w represents a positive integer (e.g., 1, 2, 3, 4, 5, 8, 10, 12, or 15, or more). Examples of divalent organic groups $R^7$ include: the divalent groups

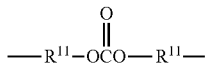

wherein each $R^{11}$ independently represents an alkylene group having from 2 to 4 carbon atoms, preferably ethan-1,2-diyl or propan-1,2-diyl;

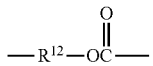

wherein $R^{12}$ represents an alkylene group having from 2 to 11 carbon atoms, and alkylene groups having from 1 to 12 carbon atoms, preferably 1 to 6 carbon atoms, and more preferably 1 to 4 carbon atoms. In some preferred embodiments, $R^7$ is an alkylene group having 2 to 4 carbon atoms, more preferably ethylene or propylene.

The divalent segments d) are represented by the formula

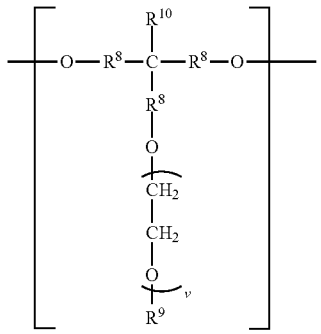

wherein each $R^8$ independently represents an alkylene group having from 1 to 8 carbon atoms, preferably 1 to 6 carbon atoms, and more preferably 1 to 4 carbon atoms. Examples include methylene, ethylene (i.e., ethan-1,2-diyl), propan-1,2-diyl, butane-1,4-diyl, hexan-1,6-diyl, cyclohexan-1,4-diyl, and octan-1,8-diyl.

Each $R^9$ independently represents an alkyl group having from 1 to 4 carbon atoms. Examples include methyl, ethyl, propyl, isopropyl, and butyl groups.

Each $R^{10}$ independently represents H or an alkyl group having from 1 to 8 carbon atom. Examples include methyl, ethyl, propyl, isopropyl, butyl, isobutyl, pentyl, hexyl, cyclohexyl, heptyl, and octyl groups.

v represents a positive integer, preferably in the range of from 3 to 50. Examples include, 1, 2, 3, 4, 5, 6, 7, 8, 10, 15, 20, 25, 30, 35, 40, 45, 50, or more.

In some preferred embodiments, the antistatic polyurethane may further comprise divalent units e) corresponding to added chain extenders such as alkanediols and/or alkanediamines having from 1 to 8 carbon atoms, preferably 2 to 4 carbon atoms. For example, the antistatic polymer may further comprise divalent segments such as

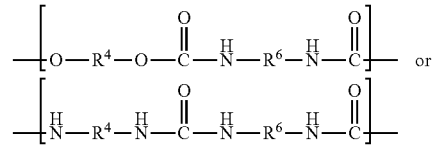

wherein $R^4$ and $R^7$ are as previously defined.

Divalent monomeric units a) to d) may be present in any amounts. In some preferred embodiments, on a relative molar basis, the antistatic polymer comprises 0.5 to 30 moles of divalent unit a) (preferably 1 to 25 moles), 40 to 70 moles of divalent unit b) (preferably 45 to 65 moles), 1 to 40 moles of divalent unit c) (preferably 6 to 30 moles), and 1 to 10 moles of divalent unit d) (preferably 1 to 6 moles).

Antistatic polyurethanes according to the present disclosure can be made, for example, by reacting at least one diisocyanate with at least one diol, preferably in the presence of a catalyst such as, e.g., dibutyltin dilaurate. Conditions and catalysts for polyurethane formation are well known to those of ordinary skill in the polyurethane art. In some preferred embodiments, a single diisocyanate is used.

The diisocyanate includes a diisocyanate represented by the formula $$OCN—R^6—NCO$$

wherein $R^6$ is as previously defined. Exemplary suitable diisocyanates include: isophorone diisocyanate (IPDI); 4,4'-methylene-bis-phenylisocyanate (MDI); hexamethylene diisocyanate (HDI); 2,4-tolylene diisocyanate (TDI); bis(4-isocyanatocyclohexyl)methane (H-MDI); 3,5,5-trimethyl-1-isocyanato-3-isocyanatomethylcyclohexane); 1,3-bis(isocyanatomethyl)cyclohexane. Other diisocyanates are described, for example, in U.S. Pat. No. 3,641,199 (Niederhauser et al.); U.S. Pat. No. 3,700,643 (Potts et al.); and U.S. Pat. No. 3,931,117 (Potts et al.). Many suitable diisocyanates are available commercially (e.g., from Bayer MaterialScience, Pittsburgh, Pa., or Dow Chemical Co., Midland, Mich.) and/or can be prepared by known methods.

A molar excess of the diisocyanate(s) is reacted with one ionic diol represented by the formula:

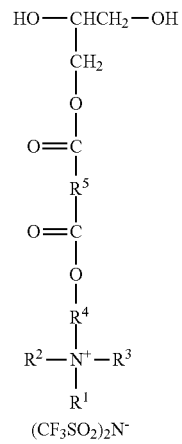

wherein $R^1$-$R^5$ are as previously defined. Diols of this type can be prepared, for example, by sequential reaction of an ionic mono-alcohol with a cyclic anhydride (e.g., malonic anhydride, succinic anhydride, valeric anhydride), and then reaction of that product with glycidol; for example, as described in the examples hereinbelow. Exemplary suitable mono-alcohols and general synthetic methods for their preparation are described in, for example, U.S. Pat. No. 6,706,920 B2 (Lamanna et al.) and include octyldimethyl-2-hydroxyethylammonium bis(trifluoromethanesulfonyl) imide. In one easy method, corresponding quaternary ammonium surfactant mono-alcohols with halide counterions can be ion exchanged to provide the bis(trifluoromethanesulfonyl)imide salts; for example using $LiN(SO_2CF_3)_2$ from 3M Company.

Reaction of the excess diisocyanate and ionic diol(s) results in an isocyanate-functional first prepolymer, which is then reacted with at least one chain extender diol independently represented by the formula

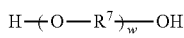

wherein $R^7$ is as previously defined. Exemplary diols include ethylene glycol, propylene glycol, butylene glycol, 1,4-dihydroxydiol, 1,6-dihydroxyhexane, 1,4-dihydroxycyclohexane, poly(alkylene oxide) diols (e.g., polyethylene glycol diols and polypropylene glycol diols), polycarbonate diols, polyester diols, polyurethane diols, and combinations thereof. Suitable polyalkylene oxide diols include, for example, polyethylene oxide diols, and polypropylene oxide diols. Suitable polycarbonate diols include, for example, those aliphatic polycarbonate diols marketed by Bayer MaterialScience AG under the trade designation "DESMOPHEN" (e.g., in grades C 1100, C 1200, C 2100, C 2200, and C 3100 XP), by Perstorp under the trade designation "OXYMER" (e.g., OXYMER M112) and 1,6-hexanediol polycarbonate, and Kuraray America under the trade designation "POLYOL" P-series and C-series.

Preferably, the isocyanate-functional first prepolymer is present in a molar excess relative to the chain extender diol, resulting in excess isocyanate groups relative to the hydroxyl groups of the chain extender diol.

If higher molecular weights are desired, various chain extenders such as, for example, substituted- or unsubstituted-alkanediols and/or alkanediamines having from 1 to 8 carbon atoms, preferably 12 to 4 carbon atoms may be reacted with any terminal isocyanate groups on the antistatic polymers/prepolymers according to the present disclosure. Examples of suitable diols and diamines include ethylene glycol, propylene glycol, 1,3-propanediol, 1,4-butanediol, 2,2-dimethylolpropionic acid, 1,2-ethanediamine, 1,3-propanediamine, and 1,6-hexanediamine.

If desired, antistatic polyurethanes according to the present disclosure can be combined with one or more conventional additives commonly used in the art such as, for example, dyes, pigments, antioxidants, ultraviolet stabilizers, flame retardants, surfactants, plasticizers, tackifiers, fillers, and mixtures thereof to provide an antistatic composition. In particular, performance enhancers (for example, polymers such as polybutylene) can be utilized to improve the antistatic characteristics in, for example, melt additive polyolefin applications.

Antistatic polyurethanes according to the present disclosure can be used in coating compositions (e.g., as dissolved or dispersed in water and/or organic solvent) or with various insulating (e.g., dielectric) materials (i.e., coated directly onto an insulating material) provided these antistatic polyurethanes are compatible with the coating and/or insulating materials. Thus, the antistatic polyurethane preferably performs well as an antistat and does not adversely affect other properties of the coating and/or insulating materials.

Antistatic polyurethanes according to the present disclosure may comprise about 0.1 to about 50 weight percent of an antistatic coating composition, based on the solids in the coating composition.

Antistatic coating compositions including an antistatic polyurethane according to the present disclosure can be applied from aqueous or organic solvents (including solutions of binders) to a variety of insulating materials including, for example, fabric, fibers, electronic components, electronic packaging, compact discs, and molded or blown objects (e.g., surgical gowns). The coating composition is preferably water-based, but may contain organic solvent. In some embodiments, the coating composition is solvent-based. Examples of solvents include ethers, esters, ketones, and alcohols.

Insulating materials that are suitable for topical treatment include materials that have relatively low surface and bulk conductivity and that are prone to static charge build-up. These materials include both synthetic and naturally-occurring polymers (or the reactive precursors thereof, for example, mono- or multifunctional monomers or oligomers) that can be either organic or inorganic in nature, as well as ceramics, glasses, and ceramic/polymer composites, ceramers, or the reactive precursors thereof.

Insulating materials that are suitable for blending with antistatic polyurethanes according to the present disclosure may include thermoplastic polymers and thermosetting compositions, for example. Suitable synthetic polymers (which can be either thermoplastic or thermoset) include commodity plastics such as, for example, poly(vinyl chloride), polyethylenes (high density, low density, very low density), polypropylene, polybutylene, and polystyrene; engineering plastics such as, for example, polyesters (including, for example, poly(ethylene terephthalate) and poly (butylene terephthalate), polyamides (aliphatic, amorphous, aromatic), polycarbonates (for example, aromatic polycarbonates such as those derived from bisphenol A), polyoxymethylenes, polyacrylates and polymethacrylates (for example, poly(methyl methacrylate)), some modified polystyrenes (for example, styrene-acrylonitrile (SAN) and acrylonitrile-butadiene-styrene (ABS) copolymers), high-impact polystyrenes (SB), fluoroplastics, and blends such as poly (phenylene oxide)-polystyrene and polycarbonate-ABS; high-performance plastics such as, for example, liquid crystalline polymers (LCPs), polyetherketone (PEK), polysulfones, polyimides, and polyetherimides; thermosets such as, for example, alkyd resins, phenolic resins, amino resins (for example, melamine and urea resins), epoxy resins, unsaturated polyesters (including so-called vinyl esters), polyurethanes, allylics (for example, polymers derived from allyl diglycol carbonate), fluoroelastomers, and polyacrylates; and the like and blends thereof. Suitable naturally occurring polymers include proteinaceous materials such as silk, wool, and leather; and cellulosic materials.

Thermoplastic and thermoset polymers, including those described above, are preferred insulating materials, as these polymers can either be topically treated with the antistat or can be combined with the antistat (in bulk) to form a blend. Melt processing of the antistat into a thermoplastic polymer is preferred, because it eliminates the use of hazardous solvents and volatile organic compounds (VOCs). Preferably, the thermoplastic polymers are melt-processable at elevated temperatures, for example, above about 150° C., more preferably above about 240° C., and even more preferably above about 280° C. Preferred thermoplastic polymers include, for example, polypropylene, polyethylene, polybutylene, copolymers of ethylene and one or more alpha-olefins (for example, poly(ethylene-butene) and poly(ethylene-octene)), polyesters, polyurethanes, polycarbonates, polyetherimides, polyimides, polyetherketones, polysulfones, polystyrenes, ABS copolymers, polyamides, fluoroelastomers, and blends thereof.

The antistatic polyurethane can also be blended with monomers, curable oligomers, or curable polymers followed by polymerization or curing to form a crosslinked thermoset polymer containing the antistat. Preferred thermoset polymers include polyurethanes, epoxy resins, and unsaturated polyesters.

Antistatic polyurethanes according to the present disclosure can further be applied to an insulating material using techniques known in the art such as, but not limited to, dip coating, spray coating, swirl coating, spin coating, extrusion hopper coating, curtain coating, gravure coating, air knife coating, and the like. The coating thickness varies as a function of the insulating material.

SELECT EMBODIMENTS OF THE PRESENT DISCLOSURE

In a first embodiment, the present disclosure provides an ionic diol represented by the formula:

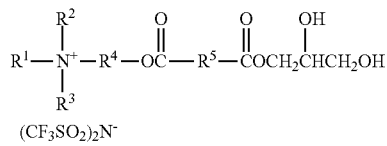

wherein
$R^1$ represents an alkyl group having from 6 to 18 carbon atoms;
$R^2$ and $R^3$ independently represent alkyl groups having from 1 to 4 carbon atoms;
$R^4$ represents an alkylene group having from 2 to 8 carbon atoms; and
$R^5$ represents an alkylene group having from 1 to 8 carbon atoms.

In a second embodiment, the present disclosure provides an ionic diol according to the first embodiment, wherein $R^1$ has from 6 to 10 carbon atoms.

In a third embodiment, the present disclosure provides an ionic diol according to the first or second embodiment, wherein $R^2$ and $R^3$ are independently methyl or ethyl.

In a fourth embodiment, the present disclosure provides an ionic diol according to any one of the first to third embodiments, wherein $R^4$ has from 2 to 4 carbon atoms.

In a fifth embodiment, the present disclosure provides an ionic diol according to any one of the first to fourth embodiments, wherein $R^5$ has from 2 to 4 carbon atoms.

In a sixth embodiment, the present disclosure provides an antistatic polyurethane having a polymer backbone comprising:
at least one divalent segment a) represented by the formula

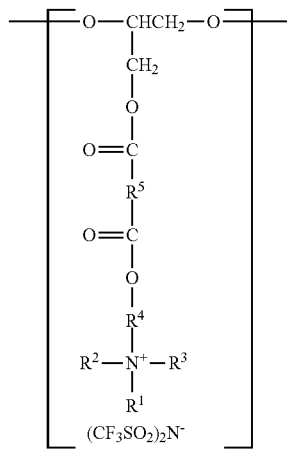

wherein
$R^1$ represents an alkyl group having from 6 to 18 carbon atoms,
$R^2$ and $R^3$ independently represent alkyl groups having from 1 to 4 carbon atoms,
$R^4$ represents an alkylene group having from 2 to 18 carbon atoms, and
$R^5$ represents an alkylene group having from 2 to 18 carbon atoms;
divalent segments b) represented by the formula

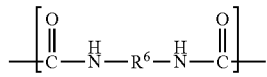

wherein
$R^6$ represents a divalent organic group having from 2 to 18 carbon atoms, wherein at least one of the divalent segments b) is adjacent to at least one of the divalent segments a);
divalent segments c) represented by the formula

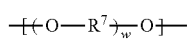

wherein
$R^7$ represents a divalent organic group having from 2 to 12 carbon atoms, and
w represents a positive integer, wherein at least one of the divalent segments c) is adjacent to at least one of the divalent segments b); and
divalent segments d) represented by the formula

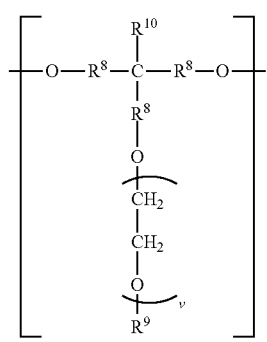

wherein
each $R^8$ independently represents an alkylene group having from 1 to 8 carbon atoms, each $R^9$ independently represents an alkyl group having from 1 to 4 carbon atoms, each $R^{10}$ independently represents H or an alkyl group having from 1 to 8 carbon atoms, and v represents a positive integer, wherein at least one of the divalent segments d) is adjacent to at least one of the divalent segments b), wherein terminal carbonyl groups on adjacent divalent segments are not directly bonded to each other, and wherein terminal —O— groups on adjacent divalent segments are not directly bonded to each other.

In a seventh embodiment, the present disclosure provides an antistatic polyurethane according to the sixth embodiment, wherein $R^1$ has from 6 to 10 carbon atoms.

In an eighth embodiment, the present disclosure provides an antistatic polyurethane according to the sixth or seventh embodiment, wherein $R^2$ and $R^3$ are independently methyl or ethyl.

In a ninth embodiment, the present disclosure provides an antistatic polyurethane according to any one of the sixth to eighth embodiments, wherein $R^4$ has from 2 to 4 carbon atoms.

In a tenth embodiment, the present disclosure provides an antistatic polyurethane according to any one of the sixth to ninth embodiments, wherein $R^5$ has from 2 to 4 carbon atoms.

In an eleventh embodiment, the present disclosure provides an antistatic polyurethane according to any one of the sixth to tenth embodiments, wherein $R^6$ has from 12 to 16 carbon atoms.

In a twelfth embodiment, the present disclosure provides an antistatic polyurethane according to any one of the sixth to eleventh embodiments, wherein $R^7$ is ethylene or propylene.

In a thirteenth embodiment, the present disclosure provides an antistatic polyurethane according to any one of the sixth to twelfth embodiments, wherein $R^8$ has from 1 to 4 carbon atoms.

In a fourteenth embodiment, the present disclosure provides a method of making an antistatic polyurethane, the method comprising steps:

a) reacting a first diol with a molar excess of a diisocyanate to form a first prepolymer, wherein the first diol is represented by the formula

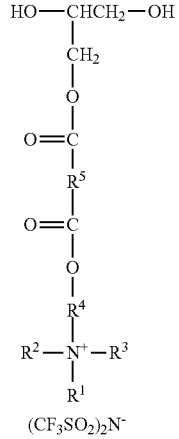

wherein $R^1$ represents an alkyl group having from 6 to 18 carbon atoms;

$R^2$ and $R^3$ independently represent alkyl groups having from 1 to 4 carbon atoms;

$R^4$ represents an alkylene group having from 2 to 18 carbon atoms $R^5$ represents an alkylene group having from 2 to 18 carbon atoms; and wherein the diisocyanate is represented by the formula

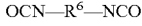

wherein $R^6$ represents a divalent organic group having from 2 to 18 carbon atoms;

b) reacting the first prepolymer with a second diol to form a second prepolymer, wherein the second diol is represented by the formula

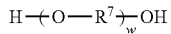

wherein $R^7$ represents a divalent organic group having from 2 to 12 carbon atoms, w represents a positive integer; and c) reacting the second prepolymer with a third diol to form the antistatic polyurethane, wherein the third diol is represented by the formula

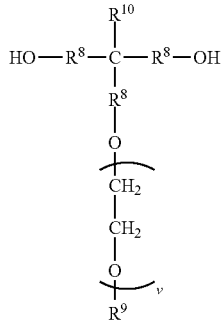

wherein each $R^8$ independently represents an alkylene group having from 1 to 8 carbon atoms, each $R^9$ independently represents an alkyl group having from 1 to 4 carbon atoms, each $R^{10}$ independently represents H or an alkyl group having from 1 to 8 carbon atoms, and v represents a positive integer.

In a fifteenth embodiment, the present disclosure provides method according to the fourteenth embodiment, wherein $R^1$ has from 6 to 10 carbon atoms.

In a sixteenth embodiment, the present disclosure provides an antistatic polyurethane according to the fourteenth or fifteenth embodiment, wherein $R^2$ and $R^3$ are independently methyl or ethyl. In a seventeenth embodiment, the present disclosure provides a method according to the fourteenth to sixteenth embodiments, wherein $R^4$ has from 2 to 4 carbon atoms.

In an eighteenth embodiment, the present disclosure provides a method according to any one of the fourteenth to seventeenth embodiments, wherein $R^5$ has from 2 to 4 carbon atoms.

In a nineteenth embodiment, the present disclosure provides a method according to any one of the fourteenth to eighteenth embodiments, wherein $R^6$ has from 12 to 16 carbon atoms.

In a twentieth embodiment, the present disclosure provides a method according to any one of the fourteenth to nineteenth embodiments, wherein $R^7$ is ethylene or propylene.

In a twenty-first embodiment, the present disclosure provides a method according to any one of the fourteenth to twentieth embodiments, wherein $R^8$ has from 1 to 4 carbon atoms.

In a twenty-second embodiment, the present disclosure provides a method according to any one of the fourteenth to twenty-first embodiments, wherein step c) provides a third prepolymer, the method further comprising d) reacting the third prepolymer with at least one of an alkanediol or an alkanediamine having from 2 to 8 carbon atoms.

In a twenty-fifth embodiment, the present disclosure provides a method according to any one of the seventeenth to twenty-fourth embodiments, wherein $R^9$ has from 12 to 16 carbon atoms.

In a twenty-third embodiment, the present disclosure provides an antistatic polyurethane made according to the method of any one of the fourteenth to twenty-second embodiments.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

TABLE OF MATERIALS USED IN THE EXAMPLES

| MATERIAL | DESCRIPTION |
| --- | --- |
| 1,4-butanediol | Aldrich Chemical Company, Milwaukee, Wisconsin |
| C-1090 POLYOL | Liquid polycarbonate polyol (Mw = 1000) from Kuraray America, Houston, Texas as POLYOL C-1090 |
| DBTDL | dibutyltin dilaurate from Sigma-Aldrich Chemical Company, St. Louis, Missouri |
| DMPA | 2,2-dimethylolpropionic acid, MW = 134.13 g/mol, Aldrich Chemical Company |
| ethylenediamine | Alfa Aesar, Ward Hill, Massachusetts |
| F-ODMHEA | octyldimethyl-2-hydroxyethylammonium bis-(trifluoromethanesulfonyl)imide prepared generally as described in Example 1 of U.S. Pat. No. 6,706,920 B2 (Lamanna et al.) |
| H12MDI | bis(4-isocyanatocyclohexyl)methane, MW = 262.35 g/mol, from Bayer MaterialScience, Pittsburgh, Pennsylvania as DESMODUR W |
| MEK | methyl ethyl ketone, Alfa-Aesar |
| PET | Polyethylene terephthalate film, 2 mils (50 micrometers) thick from 3M Company |
| succinic anhydride | Aldrich Chemical Company |
| triethylamine | Aldrich Chemical Company |
| Ymer 120 | Polymeric non-ionic dispersing diol, having the formula |

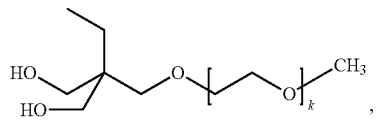

MW~1000 g/mol, obtained YMER N-120 from Perstorp Holding AB, Malmo, Sweden

All other materials were, or can be, obtained from Aldrich Chemical Company, Milwaukee, Wis.

Test Method for Measuring Surface Resistivity and Volume Resistivity

Measurements were done on a Keithley 6517A/8009 Resistivity Test Fixture (obtained from Keithley Instruments, Inc., Cleveland, Ohio) using ASTM D257-07 "Standard Test Methods for DC Resistance or Conductance of Insulating Materials" protocol. The applied voltage was 100 V. The upper limit of surface resistivity measurable by this setup is $10^{17} \Omega/\square$ (i.e., ohms per square). All tests were done under ambient conditions.

Test Method for Antistatic Testing

Static decay measurements were done on a Model 406C Electro-tech static decay meter (obtained from Electro-Tech Systems, Inc., Glenside, Pa.) using reference JKEHR008-018. Positively and negatively biased potentials of 5 kV were applied separately to each test sample, and the times required for the accumulated static charges to decay to 10% of their initial values were measured, up to a maximum of 60 sec. All tests were done under ambient conditions.

PREPARATION of IONIC DIOL A

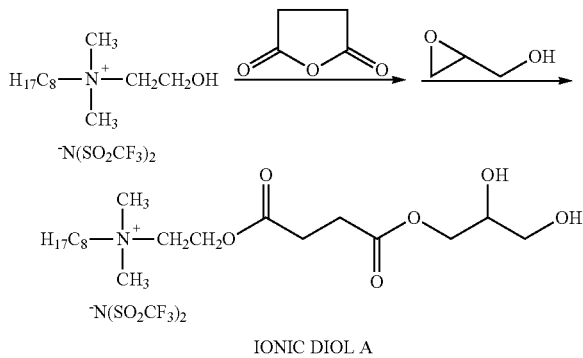

IONIC DIOL A

F-ODMHEA (46.2 g, 0.1 mol, $M_w$=462 g/mol) and succinic anhydride (10.31 g, 0.102 mol, $M_w$=100.07 g/mol) were mixed with 50 g of propylene glycol mono-methyl ether acetate (solvent), and heated to reflux for 6 hours. Glycidol (7.56 g, 0.102 mol, $M_w$=74.08 g/mol) was added, and the mixture heated to reflux for another 4 hours. The solvent was stripped off, and IONIC DIOL A was obtained.

Comparative Examples A (CEA) and B (CEB)

A polyurethane dispersion was prepared as follows. A 250 mL four-necked round bottom flask equipped with a mechanical stirrer, thermometer, condenser, and nitrogen inlet was charged with C-1090 POLYOL (28.96 g) and H12MDI (16.03 g). The reaction was carried out with stirring at 78° C. in the presence of DBDTL (0.01 wt. % based on the total solid). After 1 hour of reaction, 5.0 g of Ymer-120, 20 g MEK, and 1.62 g of F-ODMHEA were added. The reaction was continued for about two hrs. The resulting prepolymers were cooled to room temperature.

Aqueous dispersions of the prepolymers were made by slowly adding water to the polyurethane prepolymer with vigorous stirring. Once the prepolymer was dispersed, ethylenediamine (1.20 g in 5.0 g of water) was slowly added with stirring for further chain extension. The MEK was removed at 40° C. using a rotary evaporator, resulting in a dispersion of Antistatic Polyurethane A having a solids content of 30% by weight as Comparative Example A coating solution.

Comparative Example B coating solution was prepared in the same manner as Example 1, except that the coating mixture did not contain any F-ODMHEA.

Comparative Examples A and B solutions were coated on a PET film using #10 Mayer rod (nominal wet thickness=0.23 mm), and then the coatings were cured in a 120 □C oven for 3 minutes. The coated samples were tested (two samples per Example) for their antistatic properties as described above. Table 1 (below) reports the results, wherein "WNC" means would not charge.

TABLE 1

| EXAMPLE | SAMPLE | SIDE | $S_R$, ohm/square | STATIC DECAY, seconds | |
|---|---|---|---|---|---|
| | | | | +5 kV | −5 kV |
| CEA | 1 | coated | $2 \times 10^{15}$ | >60 | WNC |
| | | uncoated | $4 \times 10^{15}$ | >60 | WNC |
| | 2 | coated | $3 \times 10^{15}$ | WNC | >60 |
| | | uncoated | $2 \times 10^{15}$ | WNC | >60 |
| | 1 | coated | $2 \times 10^{15}$ | WNC | >60 |
| | | uncoated | $2 \times 10^{15}$ | WNC | >60 |
| | 2 | coated | $2 \times 10^{15}$ | WNC | >60 |
| | | uncoated | $2 \times 10^{15}$ | WNC | >60 |
| CEB | 1 | A | $2 \times 10^{15}$ | WNC | >60 |
| | | B | $2 \times 10^{15}$ | | |
| | 2 | A | $3 \times 10^{15}$, $6 \times 10^{15}$ | WNC | >60 |
| | | B | $2 \times 10^{15}$ | | |

Comparative Examples C and D (CED)

A polyurethane dispersion was prepared as follows. A 250 mL four-necked round bottom flask equipped with a mechanical stirrer, thermometer, condenser and nitrogen inlet was charged with 50.31 g of C-1090 POLYOL, 3.0 g of DMPA, 5.59 g of Ymer 120, and 41.09 g of H12MDI. The reaction was carried out under stirring at 78° C. in the presence of DBDTL (0.01 wt. % based on the total solids). After 1 hour reaction, 2.15 g of 1,4-butanediol, 20 g of MEK, and 1.62 g of F-ODMHEA were added. The reaction was carried out for about 2 hours, cooled to room temperature, and neutralized with 2.27 g of triethylamine over 30 minutes resulting in a prepolymer.

Aqueous dispersions were accomplished by slowly adding water to the prepolymer with vigorous stirring. Once the prepolymer was dispersed, ethylenediamine (2.86 g in 5.0 g water) was slowly added for further chain extension under the stirring. MEK was removed at 40° C. on a rotary evaporator, resulting in a polyurethane dispersion with a solid content of 30% by weight as Comparative Example C coating solution.

Comparative Example D coating solution was prepared in the same manner as Comparative Example C coating solution, except that it did not contain F-ODMHEA.

Comparative Examples C and D solutions were coated on a PET film using 410 Mayer bar, and then the coatings were cured in a 120 □C oven for 3 minutes. The coated samples were tested for their antistatic properties as described above. Table 2 (below) reports the results, wherein "WNC" means would not charge.

TABLE 2

| EXAMPLE | SAMPLE | SIDE | $S_R$, ohm/square | $V_R$, ohm-cm | STATIC DECAY, seconds | |
|---|---|---|---|---|---|---|
| | | | | | +5 kV | −5 kV |
| CEC | 1 | coated | $2.0 \times 10^{13}$ | $2 \times 10^{15}$ | 47.96 | 42.99 |
| | | uncoated | $1 \times 10^{15}$ | $1 \times 10^{16}$ | 38.16 | 31.69 |
| CED | 1 | A | $1.5 \times 10^{16}$ | $5 \times 10^{16}$ | WNC | WNC |
| | | B | $4 \times 10^{16}$ | $3 \times 10^{16}$ | WNC | WNC |

Example 1

H-12MDI (20.65 g), C-1090 POLYOL (21.14 g), Ymer 120 (2.5 g), and DBTDL (0.03 g) were charged into a 250 ml flask and heated to 80° C. for 2 hours under stirring. Then, 3.2 g of 1,4-butanediol, 10.0 g of IONIC DIOL A, 50.0 g of MEK were added and the mixture was held at 70-80° C. for 2 hours. A polyurethane solution with a high viscosity was obtained. The coating solution was coated on a PET film using a #10 Mayer rod, and then the coating was cured in a 120° C. oven for 3 minutes.

The coated samples (two samples per Example) were tested for their antistatic properties as described above. Table 3, below summarizes the results.

TABLE 3

| EXAMPLE | SAMPLE | SIDE | $S_R$, ohm/square | $V_R$, ohm-cm | STATIC DECAY, seconds | |
|---|---|---|---|---|---|---|
| | | | | | +5 kV | −5 kV |
| EX1 | 1 | coated | $2.9 \times 10^{12}$ | $2 \times 10^{15}$ | 6.75 | 6.84 |
| | | uncoated | $5 \times 10^{15}$ | $3 \times 10^{15}$ | 5.91 | 6.04 |
| | 2 | coated | $2.1 \times 10^{12}$ | $6 \times 10^{15}$ | 5.55 | 5.39 |
| | | uncoated | $2 \times 10^{15}$ | $5 \times 10^{15}$ | 5.03 | 5.14 |

Example 2 (EX2)

H12MDI (18.93 g), 10.0 g of C-1090 POLYOL, 2.5 g of Ymer 120, and 0.03 g of DBTDL were charged into a 250 mL flask, and heated to 80° C. for 2 hours with stirring, Then, 2.94 g of 1,4-butanediol, 15 g of IONIC DIOL A, and 50.0 g of MEK were charged and the mixture was held at 70-80° C. for 2 hours. A polyurethane solution with a high viscosity was obtained. The solution was coated on a PET film using #10 Mayer bar, and then the coating was cured in a 120 □C oven for 3 minutes.

The coated samples (two samples per Example) were tested for their antistatic properties as described above. Table 4 (below) reports the results.

TABLE 4

| EXAMPLE | SAMPLE | SIDE | $S_R$, ohm/square | $V_R$, ohm-cm | STATIC DECAY, seconds | |
|---|---|---|---|---|---|---|
| | | | | | +5 kV | −5 kV |
| EX2 | 1 | coated | $1.3 \times 10^{12}$ | $2 \times 10^{16}$ | 3.83 | 3.73 |
| | | uncoated | $3 \times 10^{16}$ | $2 \times 10^{15}$ | | |
| | 2 | coated | $1.4 \times 10^{12}$ | $4 \times 10^{15}$ | 3.83 | 3.58 |
| | | uncoated | $5 \times 10^{15}$ | $3 \times 10^{15}$ | | |

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. An ionic diol represented by the formula:

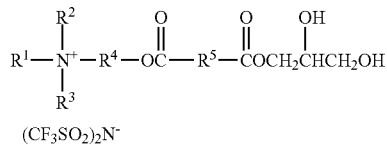

(CF$_3$SO$_2$)$_2$N$^-$ wherein
- R$^1$ represents an alkyl group having from 6 to 18 carbon atoms;
- R$^2$ and R$^3$ independently represent alkyl groups having from 1 to 4 carbon atoms;
- R$^4$ represents an alkylene group having from 2 to 8 carbon atoms; and
- R$^5$ represents an alkylene group having from 1 to 8 carbon atoms.

2. The ionic diol of claim 1, wherein R$^1$ has from 6 to 10 carbon atoms.

3. The ionic diol of claim 1, wherein R$^2$ and R$^3$ are independently methyl or ethyl.

4. The ionic diol of claim 1, wherein R$^4$ has from 2 to 4 carbon atoms.

5. The ionic diol of claim 1, wherein R$^5$ has from 2 to 4 carbon atoms.

6. An antistatic polyurethane having a polymer backbone comprising:

at least one divalent segment a) represented by formula

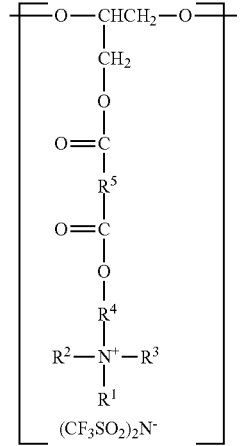

wherein
- R$^1$ represents an alkyl group having from 6 to 18 carbon atoms,
- R$^2$ and R$^3$ independently represent alkyl groups having from 1 to 4 carbon atoms,
- R$^4$ represents an alkylene group having from 2 to 18 carbon atoms, and
- R$^5$ represents an alkylene group having from 2 to 18 carbon atoms;

divalent segments b) represented by the formula

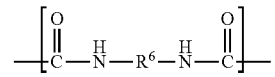

wherein
- R$^6$ represents a divalent organic group having from 2 to 18 carbon atoms, wherein at least one of the divalent segments b) is adjacent to at least one of the divalent segments a);

divalent segments c) represented by the formula

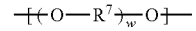

wherein
- R$^7$ represents a divalent organic group having from 2 to 12 carbon atoms, and
- w represents a positive integer, wherein at least one of the divalent segments c) is adjacent to at least one of the divalent segments b); and divalent segments d) represented by the formula

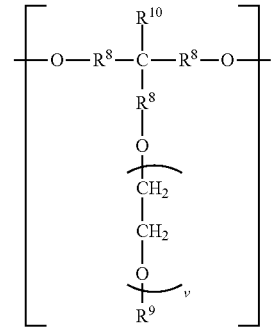

wherein
- each R$^8$ independently represents an alkylene group having from 1 to 8 carbon atoms,
- each R$^9$ independently represents an alkyl group having from 1 to 4 carbon atoms,
- each R$^{10}$ independently represents H or an alkyl group having from 1 to 8 carbon atoms, and
- v represents a positive integer, wherein at least one of the divalent segments d) is adjacent to at least one of the divalent segments b), wherein terminal carbonyl groups on adjacent divalent segments are not directly bonded to each other, and wherein terminal —O— groups on adjacent divalent segments are not directly bonded to each other.

7. The antistatic polyurethane of claim 6, wherein R$^1$ has from 6 to 10 carbon atoms.

8. The antistatic polyurethane of claim 6, wherein R$^2$ and R$^3$ are independently methyl or ethyl.

9. The antistatic polyurethane of claim 6, wherein R$^4$ has from 2 to 4 carbon atoms.

10. The antistatic polyurethane of claim 6, wherein R$^5$ has from 2 to 4 carbon atoms.

11. The antistatic polyurethane of claim 6, wherein R$^6$ has from 12 to 16 carbon atoms.

12. The antistatic polyurethane of claim 6, wherein R7 is ethylene or propylene.

13. The antistatic polyurethane of claim 6, wherein $R^8$ has from 1 to 4 carbon atoms.

14. A method of making an antistatic polyurethane, the method comprising steps:
   a) reacting a first diol with a molar excess of a diisocyanate to form a first prepolymer, wherein the first diol is represented by formula

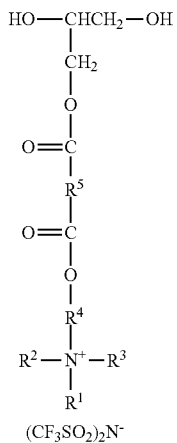

(i)

wherein
  $R^1$ represents an alkyl group having from 6 to 18 carbon atoms;
  $R^2$ and $R^3$ independently represent alkyl groups having from 1 to 4 carbon atoms;
  $R^4$ represents an alkylene group having from 2 to 18 carbon atoms
  $R^5$ represents an alkylene group having from 2 to 18 carbon atoms; and
wherein the diisocyanate is represented by the formula

OCN—$R^6$—NCO wherein $R^6$ represents a divalent organic group having from 2 to 18 carbon atoms;
  b) reacting the first prepolymer with a second diol to form a second prepolymer, wherein the second diol is represented by the formula

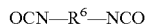

wherein
  $R^7$ represents a divalent organic group having from 2 to 12 carbon atoms,
  w represents a positive integer; and
  c) reacting the second prepolymer with a third diol to form the antistatic polyurethane,
wherein the third diol is represented by the formula

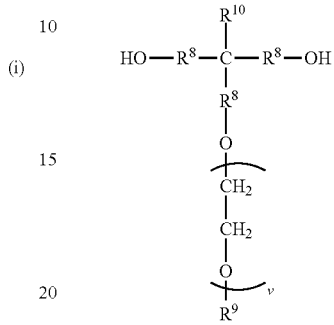

wherein
  each $R^8$ independently represents an alkylene group having from 1 to 8 carbon atoms,
  each $R^9$ independently represents an alkyl group having from 1 to 4 carbon atoms,
  each $R^{10}$ independently represents H or an alkyl group having from 1 to 8 carbon atoms, and
  v represents a positive integer.

15. The method of claim 14, wherein $R^1$ has from 6 to 10 carbon atoms.

16. The method of claim 14, wherein $R^2$ and $R^3$ are independently methyl or ethyl.

17. The method of claim 14, wherein $R^4$ has from 2 to 4 carbon atoms.

18. The method of claim 14, wherein $R^5$ has from 2 to 4 carbon atoms.

19. The method of claim 14, wherein $R^6$ has from 12 to 16 carbon atoms.

20. The method of claim 14, wherein $R^7$ is ethylene or propylene.

21. The method of claim 14, wherein $R^8$ has from 1 to 4 carbon atoms.

22. The method of claim 14, wherein step c) provides a third prepolymer, the method further comprising d) reacting the third prepolymer with at least one of an alkanediol or an alkanediamine having from 2 to 8 carbon atoms.

23. An antistatic polyurethane made according to the method of claim 14.

* * * * *

UNITED STATES PATENT AND TRADEMARK OFFICE
CERTIFICATE OF CORRECTION

PATENT NO. : 10,308,753 B2
APPLICATION NO. : 15/532881
DATED : June 4, 2019
INVENTOR(S) : Yu Yang Page 1 of 1

It is certified that error appears in the above-identified patent and that said Letters Patent is hereby corrected as shown below:

In the Specification

Column 15
Line 45, Delete "octyldimethy1-" and insert -- octyldimethyl- --, therefor.

Column 17
Line 63, Delete "410" and insert -- #10 --, therefor.

In the Claims

Column 21
Line 9, In Claim 14, after "by" insert -- the --.

Signed and Sealed this
Twenty-eighth Day of January, 2020

Andrei Iancu
*Director of the United States Patent and Trademark Office*